(12) United States Patent  
Pipelka

(10) Patent No.: US 8,137,332 B2
(45) Date of Patent: Mar. 20, 2012

(54) CONTAINER FOR INTRODUCING AT LEAST ONE NON-STERILE VESSEL IN A STERILE REGION

(76) Inventor: Friedrich Pipelka, Klosterneuburg (AT)

( * ) Notice: Subject to any disclaimer, the term of this patent is extended or adjusted under 35 U.S.C. 154(b) by 793 days.

(21) Appl. No.: 12/087,908

(22) PCT Filed: Jan. 11, 2007

(86) PCT No.: PCT/AT2007/000008
§ 371 (c)(1),
(2), (4) Date: Jul. 29, 2008

(87) PCT Pub. No.: WO2007/082325
PCT Pub. Date: Jul. 26, 2007

(65) Prior Publication Data
US 2009/0082752 A1  Mar. 26, 2009

(30) Foreign Application Priority Data

Jan. 18, 2006 (AT) .................................. A 74/2006
Apr. 13, 2006 (AT) ................................ A 643/2006

(51) Int. Cl.
*A61B 19/00* (2006.01)

(52) U.S. Cl. .......................... 604/415; 604/403; 604/411

(58) Field of Classification Search ........... 604/403–416
See application file for complete search history.

(56) References Cited

U.S. PATENT DOCUMENTS 6,357,489 B1  3/2002  Zinger
6,568,434 B2  5/2003  Zinger
2003/0069538 A1  4/2003  Pfeifer et al.
2004/0199139 A1*  10/2004  Fowles et al. ................. 604/414
2005/0137566 A1  6/2005  Fowles et al.

FOREIGN PATENT DOCUMENTS

| DE | 93 00 177 | 5/1994 |
| DE | 100 05 813 | 8/2001 |
| EP | 0 565 103 | 10/1993 |
| EP | 1 287 804 | 3/2003 |
| JP | 6 125 969 | 5/1994 |
| JP | 3 114 829 | 12/2000 |
| WO | WO 03/039632 | 5/2003 |

OTHER PUBLICATIONS

International Search Report.
Translation of Search Report to A 643/2006.

* cited by examiner

*Primary Examiner* — Tatyana Zalukaeva
*Assistant Examiner* — Philip R Wiest
(74) *Attorney, Agent, or Firm* — Collard & Roe, P.C.

(57) ABSTRACT

The invention relates to a container (5) for receiving at least one non-sterile vessel (1, 1'), in particular a pierceable ampoule with a pierceable rubber stopper (3), containing a removable substance (2, 2'), and for introducing the at least one vessel (1, 1') into a sterile region (I), said container comprising at least two interconnectable parts (6, 7) which, in their interconnected state, are designed to receive the at least one vessel (1, 1'), one container part (7) including at least one means (11, 11') for removing the respective substance (2, 2') from the at least one vessel (1, 1'). To create such a container (5) which can be produced at low costs and is easy to handle, said container parts (6, 7) are surrounded by a removable envelope (10) which consists of at least two parts (8, 9).

23 Claims, 8 Drawing Sheets

CONTAINER FOR INTRODUCING AT LEAST ONE NON-STERILE VESSEL IN A STERILE REGION

CROSS REFERENCE TO RELATED APPLICATIONS

This application is the National Stage of PCT/AT2007/000008 filed on Jan. 11, 2007, which claims priority under 35 U.S.C. §119 of Austrian Application No. A 74/2006 filed on Jan. 18, 2006 and Austrian Application No. A 643/2006 filed on Apr. 13, 2006. The international application under PCT article 21(2) was not published in English.

The invention relates to a container for receiving at least one non-sterile vessel containing a removable substance, and for introducing the at least one vessel into a sterile region, the container comprising at least two interconnectable parts which, when in their interconnected state, are designed to receive the at least one vessel, one container part including a means for removing the respective substance from the at least one vessel.

The term substance may comprise medicinal liquid, yet also dry substances which are mixed by means of a liquid solvent prior to their application. Also substances as are used e.g. in industry under clean room conditions are conceivable. The invention is particularly directed to the receiving of containers having pierceable rubber stoppers and containing an appropriate substance.

Because of the sensitive contents of such vessels, such vessels, in particular pierceable ampouls, are not sterilizable. Such non-sterile vessels are not allowed to be introduced into the sterile region, e.g. an operating room. Therefore, usually the substance contained in the non-sterile vessel is transferred into the sterile region by means of syringes and pierceable cannulas and/or by resorting to special transfer units. This procedure will be described in more detail further on. Handling in most instances requires at least one person in the sterile and one person in the non-sterile region and, therefore, is particularly complex and, thus, disadvantageous.

A device for handling a vessel comprising a liquid medicinal substance of the present type is known from U.S. Pat. No. 6,568,434 B2. In that case, the vessel comprising the medicinal substance is arranged between two container parts which become interconnected. One container part comprises a means for removing the liquid from the container in the form of a needle. Handling of the container during the transfer from the non-sterile region into the sterile region is, however, still rather complex.

Therefore, the present invention has as its object to provide an above-mentioned container with which at least one non-sterile vessel which contains a substance can be introduced into a sterile region without the risk of contamination. The construction of the container shall be as simple and inexpensive as possible so as to enable an economical application also as a disposable product. Moreover, the container shall be as easy to handle as possible.

The object according to the invention is achieved by an above-indicated container in which the container parts are enveloped by a removable envelope consisting of at least two parts. According to the invention, the at least one non-sterile vessel with the respective substance is introduced in the non-sterile region into the container that is made up of two parts. Subsequently, the envelope is removed without touching the parts of the container, and the—now envelope-free—container which has been sterilized is introduced into the sterile region. Via the at least one means for removing the respective substance from the at least one vessel, which means may be designed in various ways, the respective substance is now removed from the at least one non-sterile vessel in the sterile region and used as required. When several vessels are contained within the container, the substances may also be removed simultaneously and mixed during their removal. The container according to the invention is comparatively inexpensive to produce and, moreover, easy to employ.

The removable envelope made up of at least two parts preferably is at least partially formed of an elastic material, in particular an elastic synthetic material. When using such stretchable materials, the envelope can be arranged easily over the parts of the container and removed therefrom just as easily before the container is transferred into the sterile region.

To facilitate removal of the envelope, a projection may be provided on each part of the envelope, by means of which projection the envelope can be gripped and pulled off.

According to a further feature of the invention, the envelope parts comprise ring elements which, in the closed state of the container, preferably contact each other. These ring elements may be made of a harder material than the remaining envelope and facilitate arranging the envelope over the container and removing it therefrom.

To prevent an undesired removal of the envelope parts from the container, the envelope parts may comprise elements for a releasable connection with the container parts, which are formed by complementarily shaped elements on the container parts and on the envelope parts, for instance by grooves and by corresponding bulges. Before the envelope parts are removed from the container parts, these releasable connecting elements must be opened, or overcome, respectively.

A further advantage can be achieved if a means for releasing the connecting elements when the container is completely closed are provided, which means are formed by complementarily shaped inclined end faces of the envelope parts, and of their ring elements, respectively, so that, when the container is completely closed, the connecting elements of the envelope parts are releasable with the container parts. Consequently, when interconnecting the container parts after the at least one vessel has been received therein, the connection between the envelope parts and the container parts is automatically released and, thus, removal of the envelope will become possible more easily.

When closing the container parts, the mutually abutting inclined end faces of the envelope parts with the simultaneous shifting will cause a radial movement of the latter, by which a release of the connecting elements becomes possible.

The container may be comprised of at least two substantially equally sized container parts. By this, handling becomes easier, since on both parts of the container sufficient space will be available for the fingers of the manipulating personnel. This relates to the common size of the pierceable ampoules which have a diameter of 20 mm and a height of 50 mm, e.g. An application for several vessels and for other vessels of different sizes and shapes is, of course, also conceivable.

The container parts may be interconnectable via a plug-in connection. Such a plug-in connection can be produced in a particularly simple manner and also operated easily.

Likewise, it is possible to interconnect the container parts via a thread, the thread for an easy handling ideally having only a fraction of a 360° rotation, e.g. 900 or 1800.

In order to prevent an unintentional separation of the interconnected container parts of the container, snap noses or the like may be provided, which snap noses must be overcome prior to a separation of the container parts. Likewise, for ensuring a first opening of the parts of the containers, certain means may be provided which will be destroyed, e.g. torn up, during an opening.

Particularly for a use with just one vessel which has the shape of a cylindrical pierceable ampoule, the container parts preferably are cylindrically shaped.

To allow for a simple, rapid and inexpensive production, the container parts and the envelope parts preferably are made of synthetic material.

In order to allow observing the at least one vessel arranged in the container, or its respective content, respectively, the container parts and the envelope parts preferably are made of a transparent synthetic material. It is, of course, also possible to produce only one part of the container of a transparent synthetic material.

To enable sterilization of the container, the synthetic material preferably is capable of being sterilized, in particular sterilized by gamma radiation.

In this case, the parts of the container and the envelope parts may, e.g., be made of polyolefins, in particular polypropylene or polyethylene. Basically, however, all synthetic materials are possible for producing the container.

According to a further feature of the invention, the container parts and the envelope parts are produced by an injection moulding process. With an appropriately high number of pieces, this method allows for a particularly inexpensive production. In this way, the product can also be used as a disposable product.

The at least one removing means arranged on one part of the container is formed by a pierceable membrane which must be pierced by the needle of a respective syringe before the opening of the at least one non-sterile vessel, in particular the pierceable rubber stopper of a pierceable ampoule, likewise is pierced by said needle.

As an alternative, the at least one removing means may also be formed by at least one needle. Appropriately manipulated, the at least one needle can be pushed through the rubber stopper of the pierceable ampoule, whereupon the substance can be removed from the vessel. What is important is that the removing means is designed such that when the envelope is removed, the substance provided in the vessel cannot be contaminated before the container is transferred into the sterile region. This may, e.g., be made by means of a closing cap or the like provided in the removing means.

Preferably, such at least one needle is made of a synthetic material. With synthetic material needles, the risk of injury is lower and, moreover, such synthetic material needles can be produced more easily and more inexpensively.

As an alternative, the at least one needle may, however, also be made of metal.

The element in the container formed by, e.g., at least one needle may be connected to at least one connecting member via which at least one tool for removing the substance from the vessel is connectable.

Such a connecting member may, e.g., be formed by a quick lock, in particular by a standardized quick lock, such as, e.g., a so-called Luer or Luer-Lock closing means which is standardized for connecting cannulas, syringes and infusion tubes in the medical field. Any other form of connecting means with a possibly required application device is, however, also conceivable.

Advantageously, a sterile package of the container is provided, e.g. in the form of a blister package. This package will be opened before use, the parts of the container will be separated, the non-sterile vessel introduced, the parts assembled, and the envelope removed without touching the parts of the container and, finally, the container will be introduced into the sterile region.

The present invention will be explained in more detail by way of the accompanying drawings. Therein:

Figure 1:
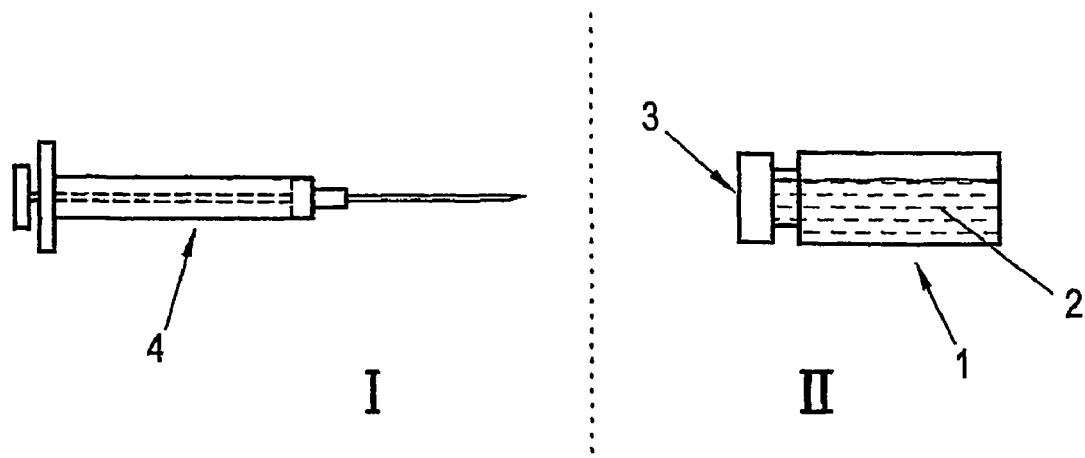
FIG. 1 shows a diagrammatic illustration of the method hitherto used for introducing a substance from a non-sterile vessel into a sterile region.

FIG. 1 shows in a diagrammatic illustration how at present a substance 2, in particular liquid, is introduced from a non-sterile vessel 1 from a non-sterile region II into a sterile region I. The vessel 1 is, in particular, a pierceable ampoule which, usually, is provided with a pierceable rubber stopper 3 for removing the substance 2. Since usually the substance 2 is a sensitive medium, the container 1 with the substance 2 contained therein is not suitable for sterilizing. For this reason, the substance 2 of the container 1 usually is introduced into the sterile region I such that at the border between sterile region I and non-sterile region II, the substance 2 is transferred from the vessel 1, for instance into a syringe 4. To this end, the rubber stopper 3 of the vessel 1 is disinfected with an alcohol swab and subsequently pierced by the needle of the syringe 4, and finally, the substance 2 is drawn into the syringe 4. Afterwards, the syringe 4 with the substance 2 in the sterile region I is, e.g., transported to the patient, and the substance 2 is applied. This procedure is comparatively complex and requires appropriate personnel, both in the non-sterile region II and also in the sterile region I, which personnel must cooperate temporally and locally. With the system described here, this temporal and local cooperation of at least two persons is no longer required. Instead of the needle on the syringe 4, also a quick lock may be provided, e.g. a Luer-Lock seal.

Figure 2:
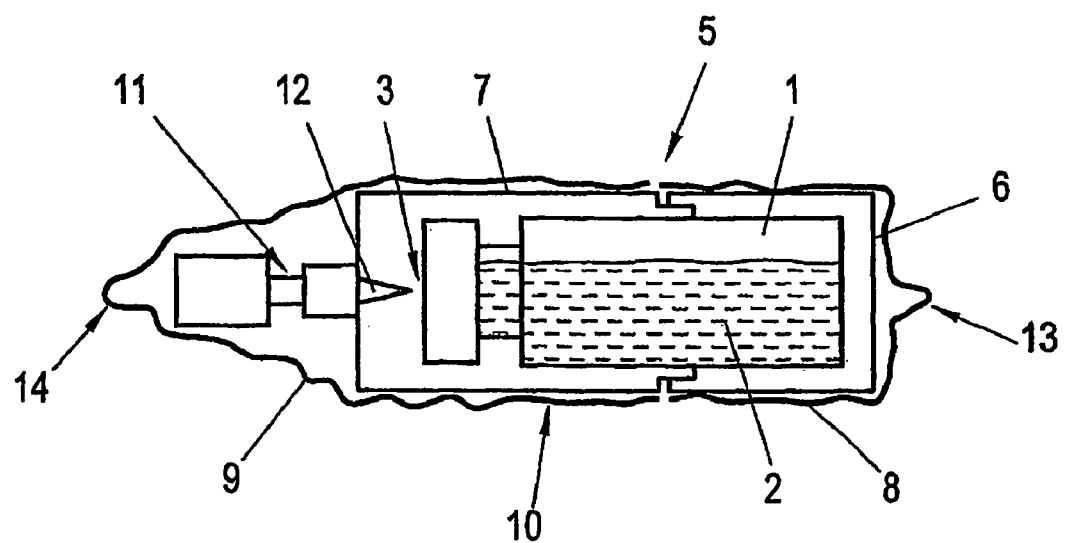
FIG. 2 shows a sectional view of an embodiment of a container according to the invention.
Figure 3A:
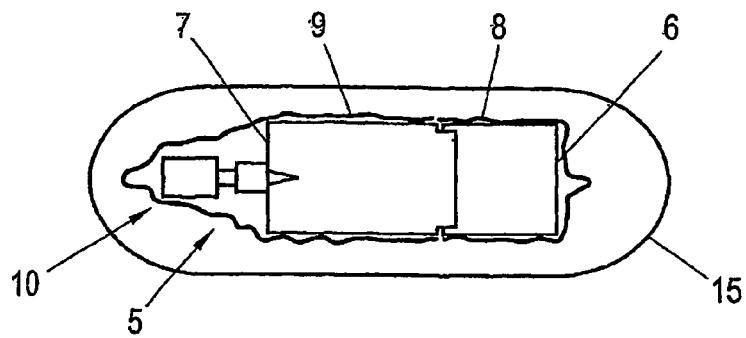
FIGS. 3a to 3d show schematic illustrations of the container for demonstrating its use.
Figure 3B:
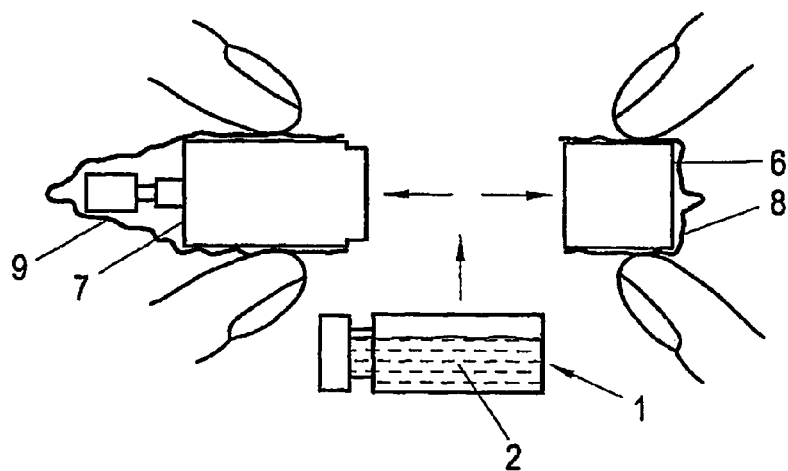
Figure 3C:
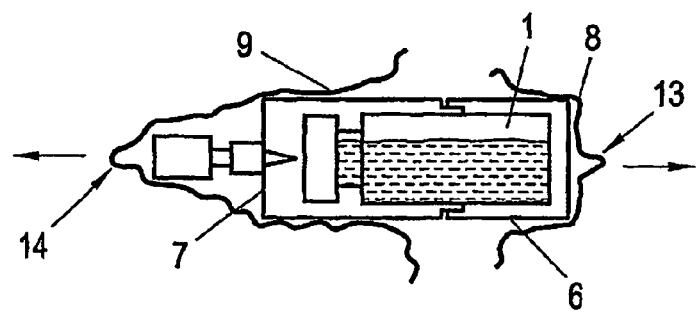
Figure 3D:
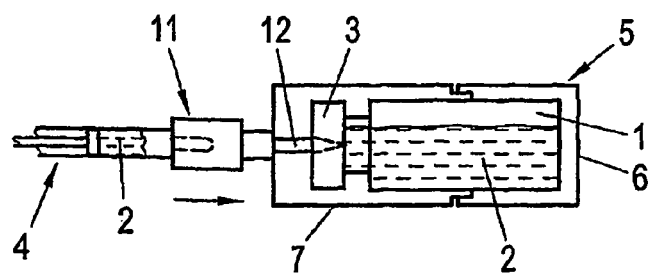

FIG. 2 shows an embodiment of the container 5 according to the invention in a sectional representation. The container 5 consists of at least two parts 6, 7, which are interconnectable and, in their interconnected state, are designed for receiving the vessel 1. In the case of a pierceable ampoule which usually is cylindrical, the container 5 also preferably is cylindrical. In addition, the container parts 6, 7 are surrounded by a removable envelope 10 comprised of at least two parts 8, 9. For allowing a removal of the substance 2 from the vessel 1, when this vessel 1 is arranged in the container 5, a means 11 for removing the substance 2 from the vessel 1 must furthermore be provided on a part 7 of the container 5. This removing means 11 may, e.g., comprise a needle 12 which pierces the rubber stopper 3 of the vessel 1. The envelope 10 comprised of at least two parts 8, 9 serves for allowing opening of the container 5 for receiving the vessel 1 without having to touch the container parts 6, 7 and, thereby, possibly contaminating them. When the vessel 1 has been received in the container 5, the envelope parts 8, 9 are removed without touching the container parts 6, 7, and the sterile container 5 with the non-sterile vessel 1 is introduced in the sterile region I. For an easier removal of the envelope parts 8, 9, appropriate projections 13, 14 may be provided. Furthermore, it is possible to widen the free ends of the envelope parts 8, 9 in trumpet shape (not illustrated), resulting in an easier handling. After insertion of the vessel 1 and connection of the container parts 6, 7 of the container 5, these widened ends of the envelope parts 8, 9 abut on each other and, thus, effectively protect the container 5 from soiling.

The container parts 6, 7 and also the envelope parts 8, 9 preferably are made of a synthetic material which shall be capable of being sterilized, in particular sterilized by gamma radiation. In order to be able to watch the content of the container 5, a transparent synthetic material is particularly suitable. The container parts 6, 7 and also the envelope parts 8, 9 may, e.g., be made of polyolefins, in particular polypropylene or polyethylene. The envelope 10 may be at least partially made of an elastic material, in particular elastic synthetic material.

The use of the container 5 according to the invention will be explained in more detail by way of FIGS. 3a to 3d. According to FIG. 3a, the container 5 comprised of parts 6 and 7 including the envelope 10 comprised of parts 8 and 9 is kept in a sterile package 15. Before being used, the sterile package 15 is opened, and the container 5 is opened by separating the container parts 6 and 7. Since the container parts 6, 7 are surrounded by the envelope parts 8, 9, the container parts 6, 7 need not be touched. According to FIG. 3b, the vessel 1 containing the sub-stance 2 is introduced into the container 5, and the container parts 6, 7 are re-united. Subsequently, according to FIG. 3c, the envelope 10 is removed by pulling off the envelope parts 8, 9. To facilitate this removal, the envelope 10 may be pulled off at the projections 13, 14. The now sterile container 5 with the non-sterile vessel 1 will then be introduced into the sterile region and may be gripped by sterile hands. In order to be able to remove the substance 2 from the vessel 1, finally a means 11 which may, e.g., be formed by a needle 12, is pierced through the rubber stopper 3 in the vessel 1 (FIG. 3d) so as to remove the substance 2 from the vessel 1. Subsequently, the substance 2 can be removed from the vessel 1 by means of an appropriate syringe 4. The piercing action of the needle 12 may be effected by shifting the removing means 11. The removing means 11 also includes a closing cap or the like which shall prevent contamination of the substance 2 in the vessel 1 after removal of the parts 8, 9 of the envelope 10.

Figure 4:
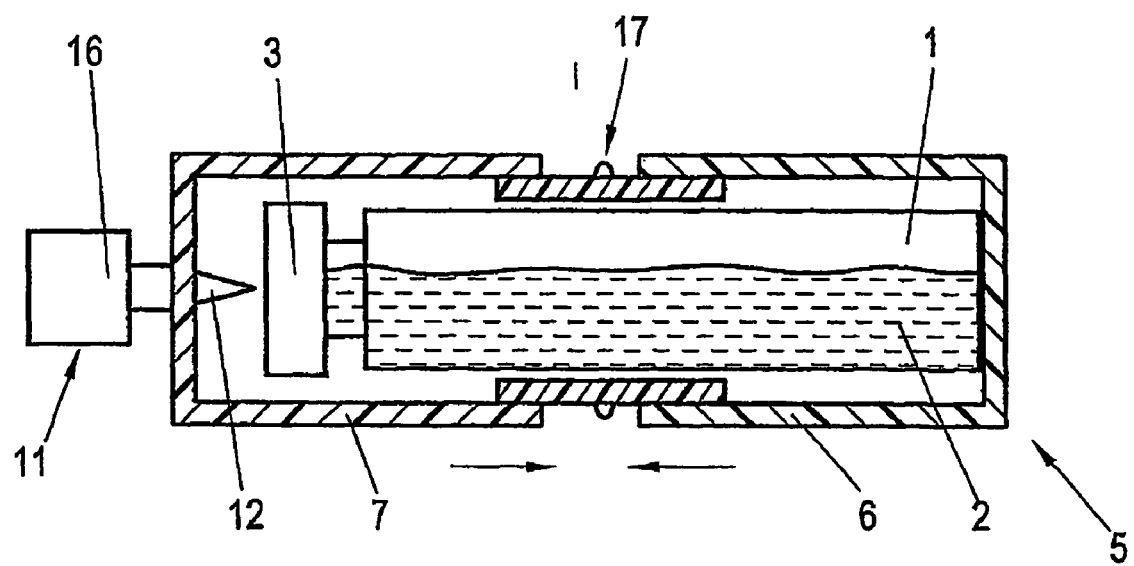
FIG. 4 shows a sectional view of a further embodiment of a container according to the invention.

FIG. 4 shows an alternative embodiment of the invention, wherein the container 5 consists of two parts 6, 7 interconnected by a plug-in connection. On one container part 7, a needle 12 is fastened, which is connected to a connecting member 16, e.g. a quick-lock, such as a Luer-Lock seal. The needle 12 is automatically pushed into the rubber stopper 3 of the vessel 1 by shifting the container parts 6, 7 in axial direction. Snap noses 17 at the connection between the container parts 6 and 7 can prevent an undesired opening of the container 5. By means of the snap noses 17, a negative effect of the non-sterile inner space of the container 5 on the sterile surroundings is prevented.

Figure 5:
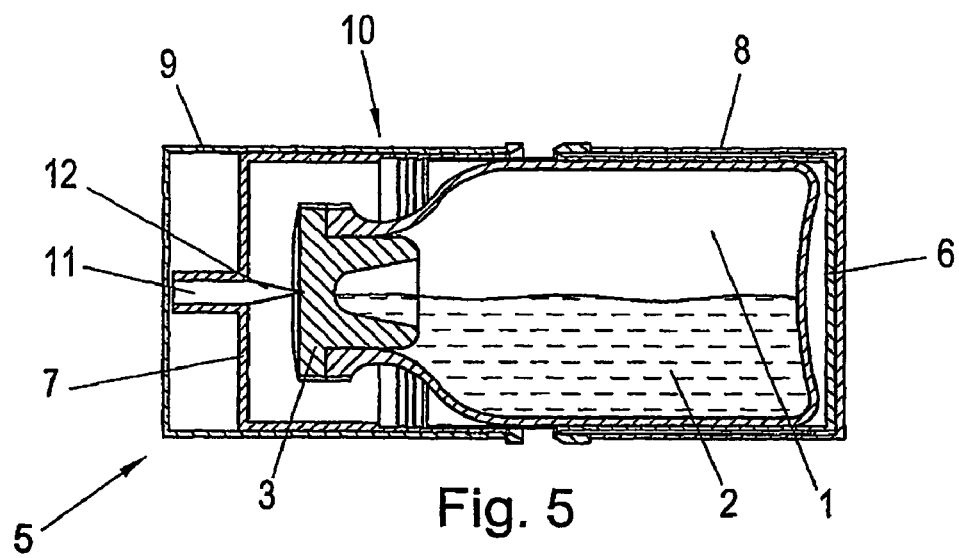
FIGS. 5 to 9 show sectional views of a further embodiment of a container according to the invention in various stages during its use.
Figure 6:
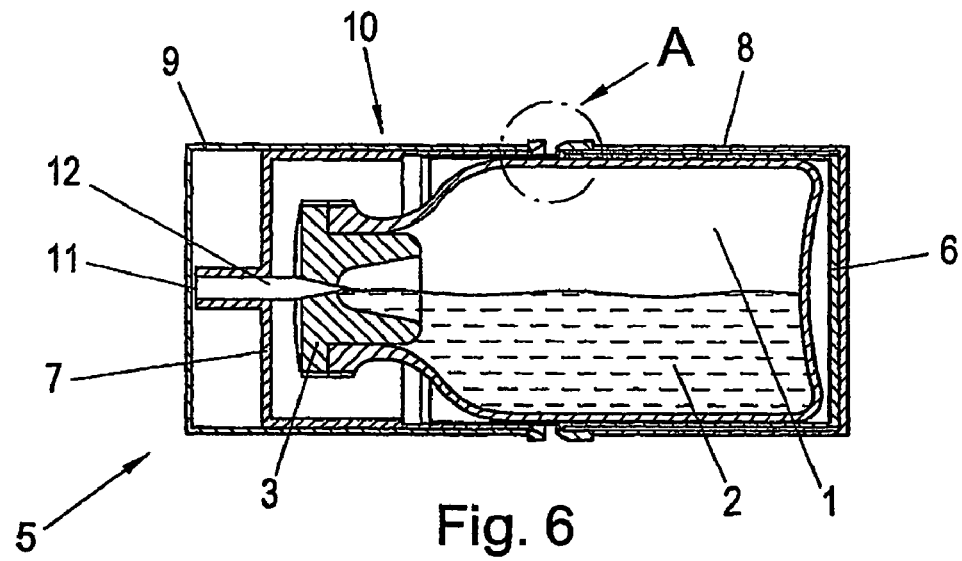
Figure 7:
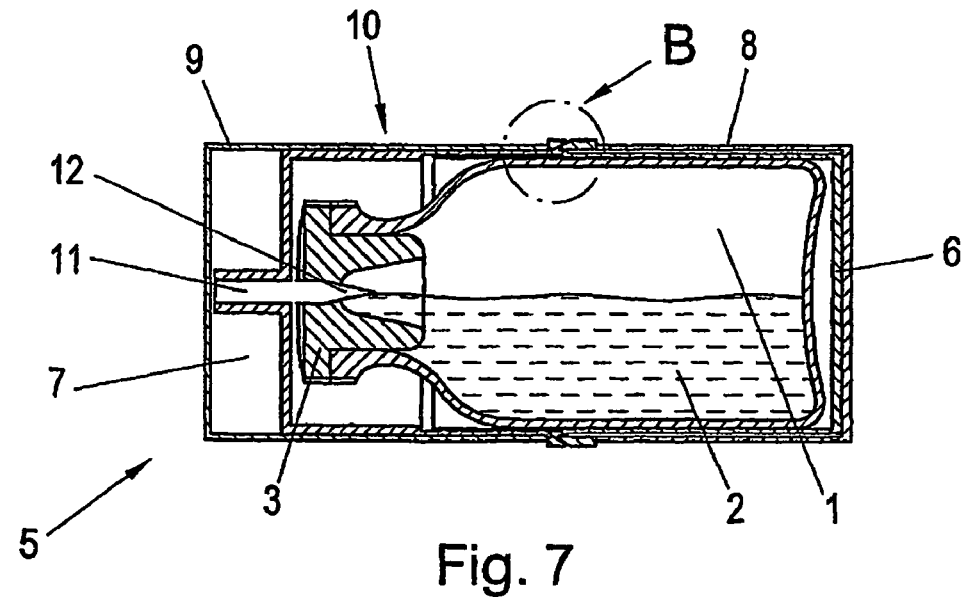
Figure 8:
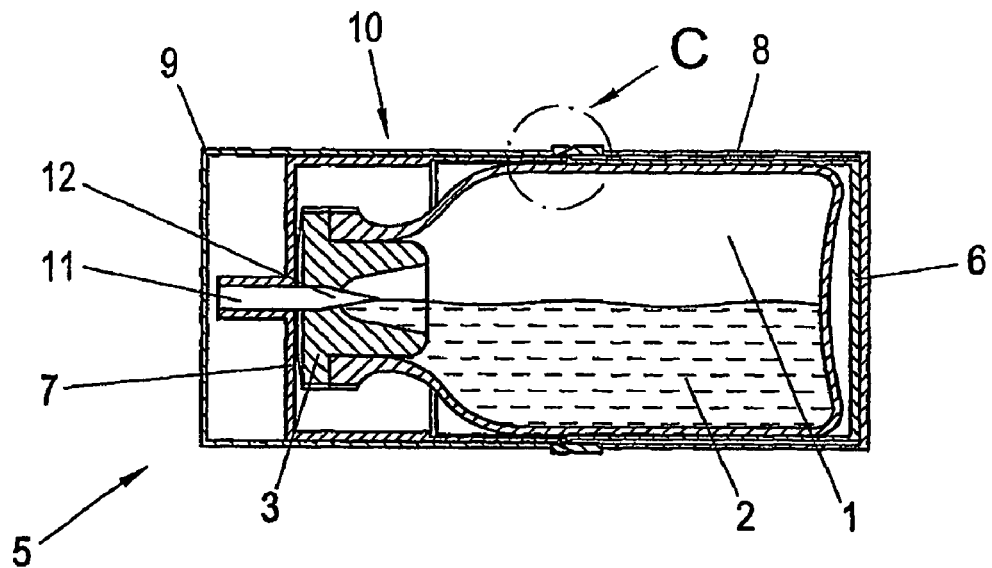
Figure 9:
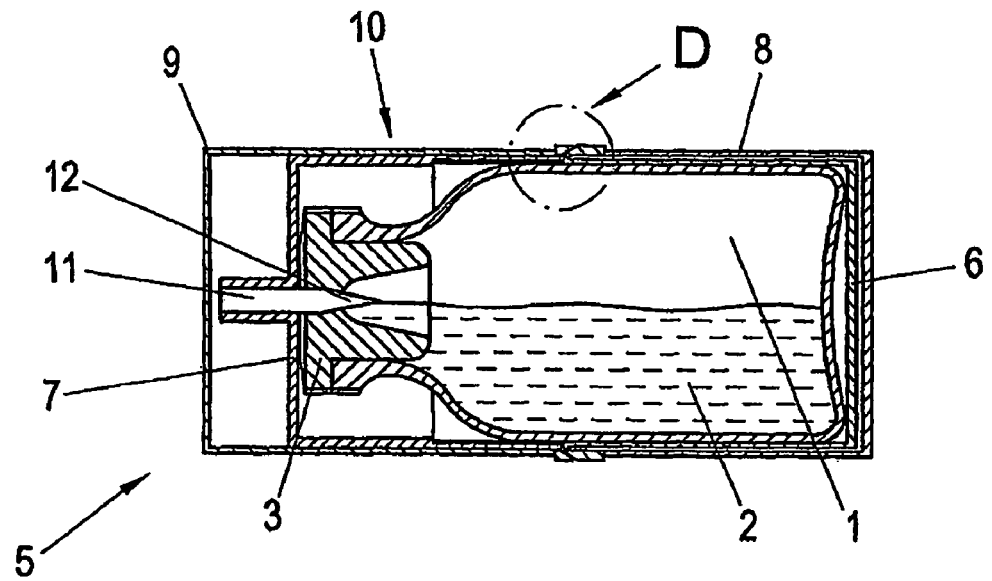

FIGS. 5 to 9 show a further embodiment of a container 5 according to the invention in a sectional representation. In contrast to the container 5 according to FIGS. 2 and 3a to 3d, the envelope 10 does not consist of parts 8, 9 of an elastic material, but of a solid material. After having introduced the non-sterile vessel 1 with the substance 2 in the container 5, the two container parts 6, 7 are shifted relative to each other, as illustrated in FIG. 5. The means 11 for removing the substance 2 from the vessel 1 which, in the case illustrated, is formed by a needle 12, is just touching the rubber stopper 3 of the vessel 1.

FIGS. 6 to 9 show the various stages until the container parts 6, 7 have been completely pushed together, where finally an unlocking of the envelope 10 from the container 5 will occur so that the envelope parts 8, 9 can be removed from the container 5 more easily, before the entire arrangement is introduced into the sterile region. In this connection, reference is made to FIGS. 10 to 13 which show the details A, B, C and D of FIGS. 6, 7, 8 and 9 in the region of the connection between the two container parts 6, 7 and the envelope parts 8, 9 in enlarged illustrations.

Figure 10:
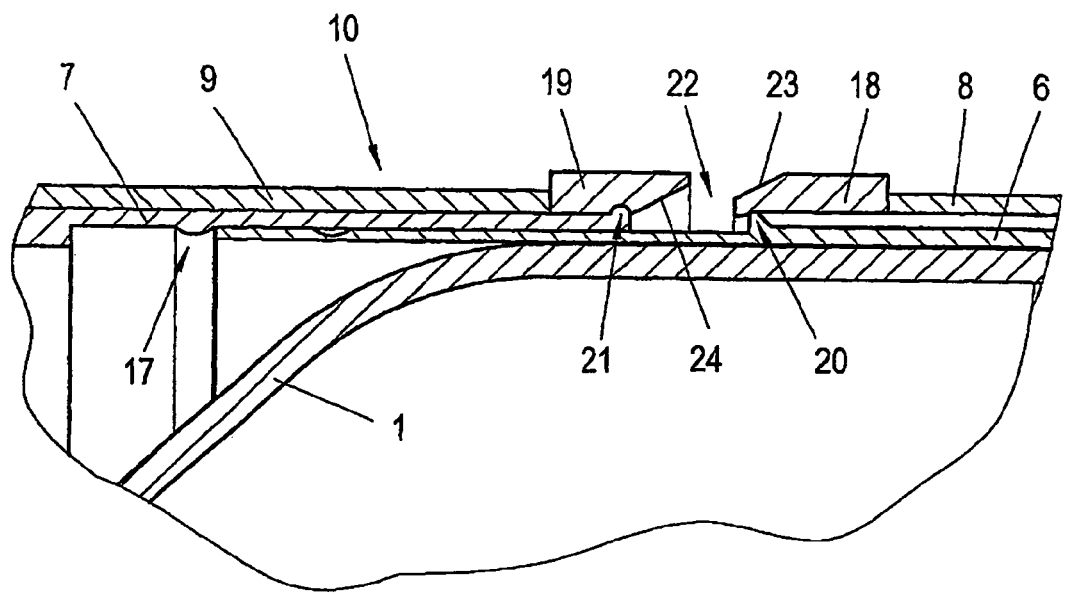
FIGS. 10 to 13 show details A to D from FIGS. 6 to 9 in enlarged illustrations.
Figure 11:
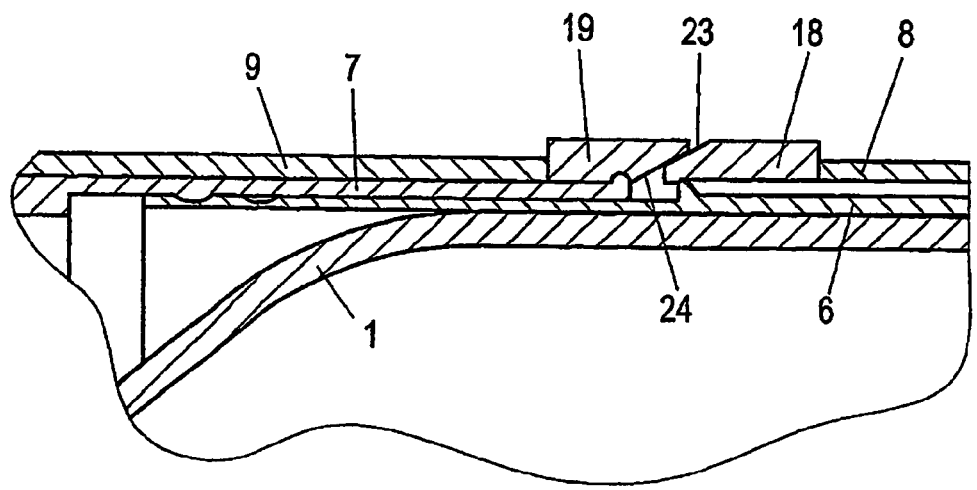
Figure 12:
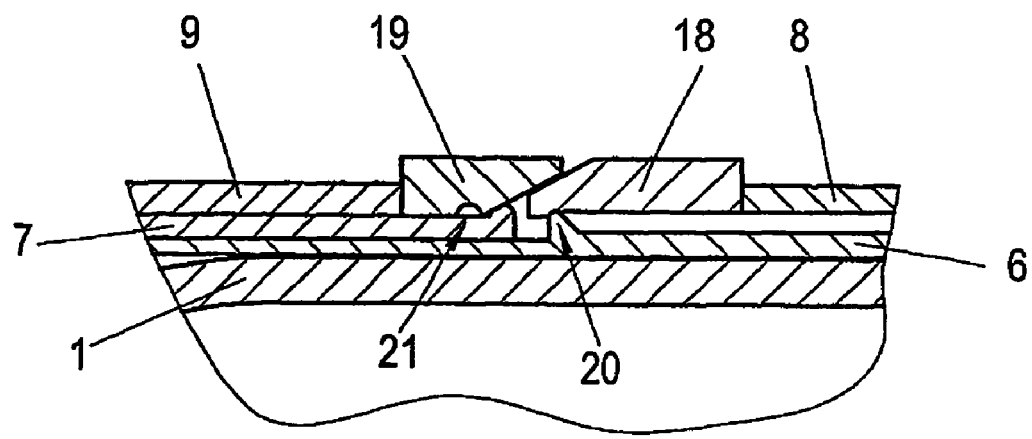
Figure 13:
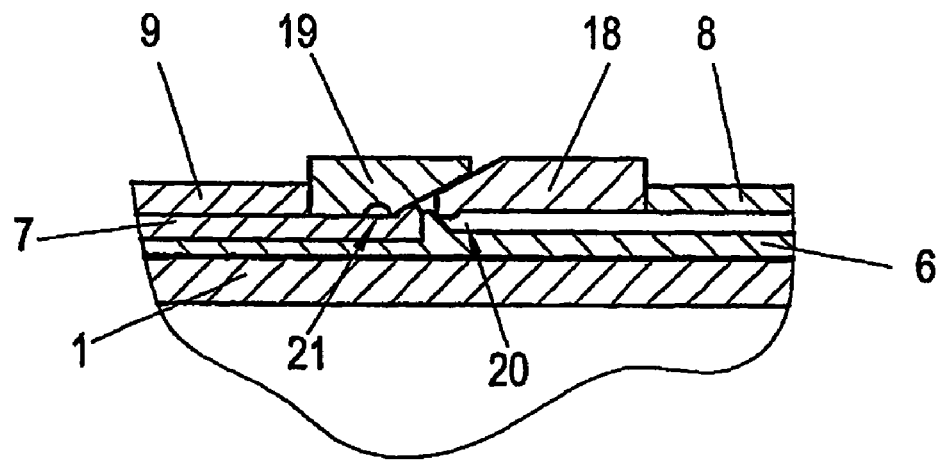

According to detail A according to FIG. 10, the container 5 consists of the two container parts 6, 7 which can be interlocked via snap noses 17, thereby preventing an undesired opening of the container (cf. also FIG. 4). The envelope 10 consists of cylindrical parts 8, 9 having ring elements 18, 19, preferably made of a more solid material than the remaining parts 8, 9. The ring elements 18, 19 of the envelope parts 8, 9 and the corresponding container parts 6, 7 have connecting elements 20, 21 according to the invention which may, e.g., be formed by complementarily shaped elements on the container parts 6, 7 and the ring elements 18, 19 of the envelope parts 8, 9. These elements 20, 21 serve for releasably connecting the envelope parts 8, 9 to the container parts 6, 7 so that an undesired removal of the envelope parts 8, 9 from the sterile container parts 6, 7 will be prevented. The ring elements 18, 19 are appropriately shaped to form a means 22 for releasing the connecting elements 20, 21. This means 22 for releasing the connecting elements 20, 21 is, e.g., realized by complementarily shaped inclined end faces 23, 24 of the ring elements 18, 19 of the envelope parts 6, 7. While the container parts 6, 7 with the envelope parts 8, 9 arranged thereon are shifted towards each other, the connecting elements 20, 21, via which the envelope parts 8, 9 are connected to the container parts 6, 7, will be opened. In the position according to FIG. 11, the inclined end faces 23, 24 of the ring elements 18, 19 come into contact. A further movement of the container parts 6, 7 towards each other will result in an opening of the connecting element 21 of the envelope part 9 with the container part 7 according to FIG. 12, and subsequently, according to FIG. 13, also in a release of the connecting element 20 between the envelope part 8 and the container part 6. In the position according to FIG. 13 and FIG. 9, respectively, the container parts 6, 7 are pressed completely towards each other, and the locking engagement between the two parts 6, 7 of the container 5 formed by the snap nose 17 will be snapped in. The connecting elements 20, 21 between the envelope parts 8, 9 and the container parts 6, 7 are released, whereby the envelope parts 8, 9 can be pushed off in a particularly simple and easy way, before the container 5 is introduced into the sterile region. The corresponding connecting elements 20, 21 and the means 22 for releasing the same may, of course, also be arranged directly on the envelope parts 8, 9 and not on the ring elements 18, 19.

The container 5 may be shaped in various ways, depending on the shape, size and number of the vessel(s) 1 to be received. Likewise, the means 11 for removing the substance 2 from the vessel 1 may be shaped in different ways.

Figure 14:
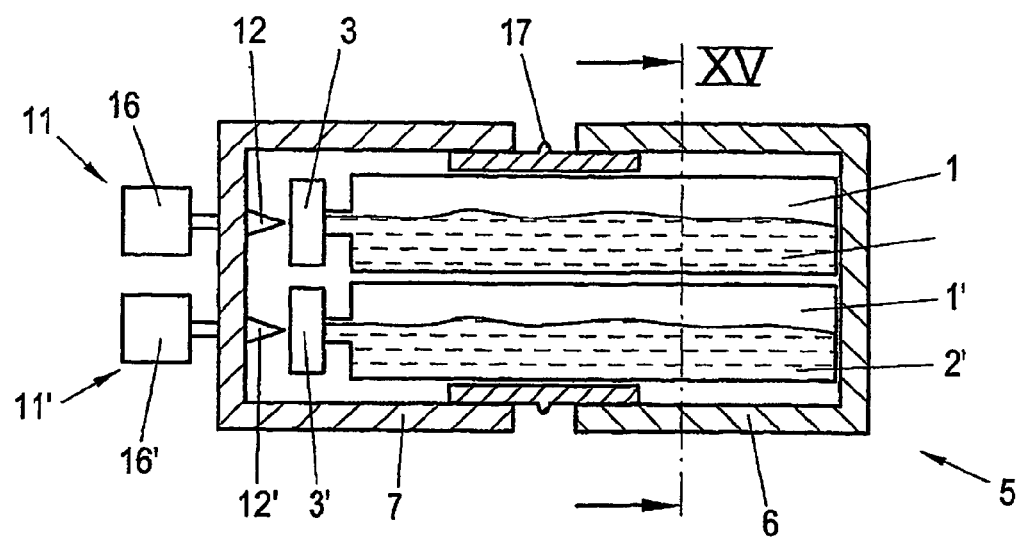
FIG. 14 shows a sectional view of a further embodiment of a container according to the invention for two vessels.
Figure 15:
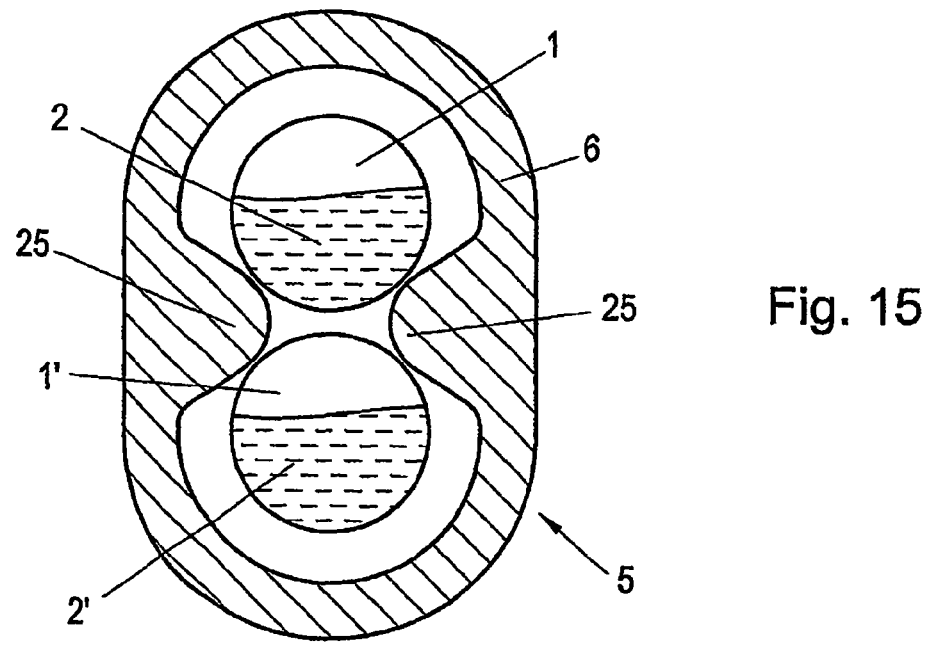
FIG. 15 shows the sectional view for the embodiment according to FIG. 14 along section line XV-XV.

FIG. 14 shows an alternative embodiment of the invention, wherein the container 5 is designed for receiving two vessels 1, 1' with substances 2, 2' contained therein. As can be seen from FIG. 15 which shows the sectional view through the container 5 along section line XV-XV of FIG. 14, the container 5 or its parts 6, 7, respectively, may be substantially oval and have corresponding receiving means for the vessels 1, 1'. In order to maintain the vessels 1, 1' substantially in their positions, bulges 25 may be arranged in part 6 and/or in part 7 of the container 5. According to the number of the vessels 1, 1', several means 11, 11' for removing the substances 2, 2' from the vessels 1, 1' are provided. These removing means 11, 11' are formed in a similar manner as in the embodiment according to FIG. 4 by at least one needle 12, 12' and one connecting member 16, 16' each. Via the connecting members 16, 16', the substances 2, 2' can be removed from the vessels 1, 1' individually or also simultaneously. Of course, also three or more vessels 1 may be arranged within a container 5.

The invention claimed is:

1. A container (5) for receiving at least one non-sterile vessel (1, 1'), in particular a pierceable ampoule with a pierceable rubber stopper (3), containing a removable substance (2, 2'), and for introducing the at least one non-sterile vessel (1, 1') into a sterile region (I), said container (5) comprising at least two interconnectable parts (6, 7) which, in their interconnected state, are designed to enclose the at least one non-sterile vessel (1, 1'), one container part (7) including at least one means (11, 11') for removing the respective substance (2, 2') from the at least one non-sterile vessel (1, 1'), wherein said container parts (6, 7) are sterile and are surrounded by a removable envelope (10) which comprises at least two parts (8, 9), wherein said sterile container parts (6, 7) for enclosing the at least one non-sterile vessel (1, 1') can be opened and closed again by gripping only the at least two parts (8, 9) of the envelope (10), said envelope being removable by pulling off the at least two parts (8, 9) of the envelope (10) before the sterile container (5) enclosing the non-sterile vessel (1, 1') is introduced into the sterile region (I).

2. The container (5) according to claim 1, wherein the envelope (10) is at least partially formed of an elastic material, in particular of an elastic synthetic material.

3. The container (5) according to claim 1, wherein a projection (13, 14) is provided on each envelope part (8, 9).

4. The container (5) according to claim 1, wherein the envelope parts (8, 9) comprise ring elements (18, 19) which, in the closed state of the container (5), preferably contact each other.

5. The container (5) according to claim 1, wherein the envelope parts (8, 9) comprise elements (20, 21) for a releasable connection with the container parts (6, 7), which are formed by complementarily shaped elements on the container parts (6, 7) and on the envelope parts (8, 9).

6. The container (5) according to claim 5, wherein a means (22) for releasing the connecting elements (20, 21), when the container (5) is completely closed, are provided, which are formed by complementarily shaped inclined end faces (23, 24) on the envelope parts (6, 7), or on ring elements (18, 19) of the at least two parts (8, 9) of the envelope (10), respectively, so that, when the container (5) is completely closed, the connecting elements (20, 21) of the at least two parts (8, 9) of the envelope (10) and of the container parts (6, 7) are releasable from each other.

7. The container (5) according to claim 1, wherein at least two, substantially equally sized container parts (6, 7) are provided.

8. The container (5) according to claim 1, wherein the container parts (6, 7) are interconnectable via plug-in connections.

9. The container (5) according to claim 1, wherein the container parts (6, 7) are interconnectable via a thread.

10. The container (5) according to claim 1, wherein snap noses or the like are provided to prevent an undesired separation of the interconnected container parts (6, 7).

11. The container (5) according to claim 1, wherein the container parts (6, 7) are cylindrically shaped.

12. The container (5) according to claim 1, wherein the container parts (6, 7) and the envelope parts (8, 9) are made of a synthetic material.

13. The container (5) according to claim 12, wherein the container parts (6, 7) and the envelope parts (8, 9) are made of a transparent synthetic material.

14. The container (5) according to claim 12, wherein the synthetic material is capable of being sterilized, in particular sterilized by gamma radiation.

15. The container (5) according to claim 12, wherein the container parts (6, 7) and the envelope parts (8, 9) are made of polyolefins, in particular polypropylene or polyethylene.

16. The container (5) according to claim 12, wherein the container parts (6, 7) and the envelope parts (8, 9) can be produced by an injection moulding process.

17. The container (5) according to claim 1, wherein the at least one removing means (11, 11') is formed by at least one pierceable membrane.

18. The container (5) according to claim 1, wherein the at least one removing means (11, 11') is formed by at least one needle (12, 12').

19. The container (5) according to claim 18, wherein the at least one needle (12, 12') is made of a synthetic material.

20. The container (5) according to claim 18, wherein the at least one needle (12, 12') is made of metal.

21. The container (5) according to claim 18, wherein the at least one element is connected to at least one connecting member (16, 16').

22. The container (5) according to claim 21, wherein the at least one connecting member (16, 16') is formed by at least one quick lock.

23. The container (5) according to claim 1, wherein a sterile package (15) is provided.

* * * * *